United States Patent
Palle et al.

(10) Patent No.: US 11,040,974 B2
(45) Date of Patent: Jun. 22, 2021

(54) CRYSTALLINE LINAGLIPTIN INTERMEDIATE AND PROCESS FOR PREPARATION OF LINAGLIPTIN

(71) Applicant: BIOCON LIMITED, Bangalore (IN)

(72) Inventors: Venkata Raghavendracharyulu Palle, Hyderabad (IN); Shanmughasamy Rajmahendra, Chennai (IN); Dharshan Jakkali Chandregowda, Chikkamagaluru (IN); Thangarasu Ponnusamy, Coimbatore (IN)

(73) Assignee: BIOCON LIMITED, Electronic (IN)

( * ) Notice: Subject to any disclaimer, the term of this patent is extended or adjusted under 35 U.S.C. 154(b) by 0 days.

(21) Appl. No.: 16/832,067

(22) Filed: Mar. 27, 2020

(65) Prior Publication Data

US 2020/0354363 A1    Nov. 12, 2020

Related U.S. Application Data (63) Continuation of application No. PCT/IB2018/057484, filed on Sep. 27, 2018.

(30) Foreign Application Priority Data

Sep. 27, 2017   (IN) .............................. 201741034292

(51) Int. Cl.
*C07D 473/06* (2006.01)
*C07D 473/04* (2006.01)

(52) U.S. Cl.
CPC ........ *C07D 473/04* (2013.01); *C07B 2200/13* (2013.01)

(58) Field of Classification Search
CPC .......................... C07D 473/06; C07B 220/13
USPC ..................................... 544/268; 514/263.21
See application file for complete search history.

(56) References Cited

U.S. PATENT DOCUMENTS

| | | |
|---|---|---|
| 7,407,955 B2 | 8/2008 | Himmelsbach et al. |
| 9,266,888 B2 | 2/2016 | Sieger et al. |

FOREIGN PATENT DOCUMENTS

| | | |
|---|---|---|
| IN | 2055/MUM/2013 A | 7/2015 |
| IN | 2250/MUM/2014 A | 1/2016 |
| WO | 2015011609 A1 | 1/2015 |

OTHER PUBLICATIONS

International Search Report for PCT/IB2018/057484, dated Apr. 4, 2019.
Anon, "Crystal Forms of Linagliptin Intermediates", ip.com Journal (2014, 14 (3A), 1-5 (No. IPCOM000234982D), Feb. 21, 2014, Coden: IJPOBX; ISSN: 1533-0001.

*Primary Examiner* — Jeffrey H Murray
(74) *Attorney, Agent, or Firm* — Katten Muchin Rosenman LLP (57) ABSTRACT

The present invention provides novel crystalline forms B1 & B2 of linagliptin intermediate of structural formula V and methods for production of novel crystalline form of linagliptin intermediate represented by the following structural formula V.

10 Claims, 6 Drawing Sheets

CRYSTALLINE LINAGLIPTIN INTERMEDIATE AND PROCESS FOR PREPARATION OF LINAGLIPTIN

RELATED APPLICATION

This application is a continuation of International Application No. PCT/IB2018/057484 filed Sep. 27, 2018, which claims the benefit of IN Patent Application 201741034292 filed Sep. 27, 2017, each of which is herein incorporated by reference in its entirety for all purposes.

TECHNICAL FIELD

The present invention relates to a method for production of linagliptin via a novel crystalline form of lingliptin intermediate. More particularly the present invention relates to novel crystalline form of linagliptin intermediate and methods for production of novel crystalline form of linagliptin intermediate represented by the following structural formula V.

Formula-V

BACKGROUND AND PRIOR ART OF THE DISCLOSURE

TRADJENTA is a dipeptidyl peptidase-4 (DPP-4) inhibitor indicated as an adjunct to diet and exercise to improve glycemic control in adults with type 2 diabetes mellitus (1.1). Linagliptin is an orally-active inhibitor of the dipeptidyl peptidase-4 (DPP-4) enzyme. It is chemically designated as 1H-purine-2,6-dione, 8-[(3R)-3-amino-1-piperidinyl]-7-(2-butyn-1-yl)-3,7-dihydro-3-methyl-1-[(4-methyl-2-quinazolinyl)methyl].

Linagliptin was disclosed in U.S. Pat. No. 7,407,955. Linagliptin, chemically 1H-Purine-2,6-dione, 8-[(3R)-3-amino-1-piperidinyl]-7-(2-butyn-1-yl)-3,7-dihydro-3-methyl-1-[(4-methyl-2quinazolinyl)methyl].

Crystalline forms A, B, C, D, E and anhydrous form A/B of Linagliptin are disclosed in U.S. Pat. No. 9,266,888.

SUMMARY OF THE INVENTION

Aspects of the present application provide a safe, simpler & economical process for the preparation of novel crystalline form of Linagliptin intermediate of Formula V and a novel process for the preparation of anhydrous form A/B of Linagliptin. Each step of the process disclosed herein are contemplated both in the context of the multistep sequences described and individually.

One aspect of the present invention is novel crystalline form B1 Linagliptin intermediate of Formula V.

Formula-V

Figure 1:
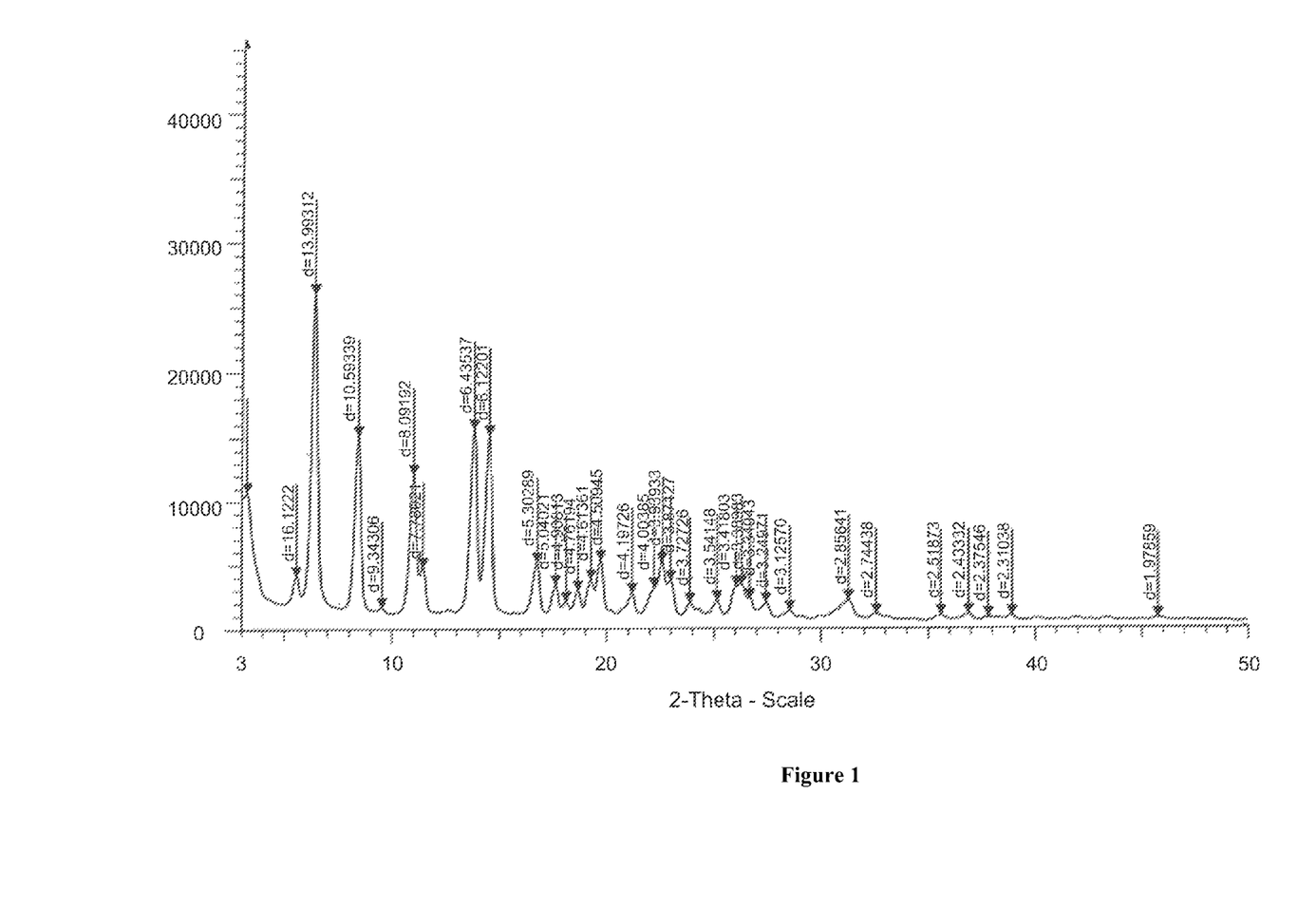

In another aspect of the present invention, the novel crystalline form B1 Linagliptin intermediate of Formula V is further characterized by PXRD having few prominent 2-theta values 3.14±0.2, 6.31±0.2, 8.33±0.2, 10.92±0.2, 13.74±0.2, 14.45±0.2, 19.67±0.2 and the PXRD pattern in accordance with the FIG. 1.

TABLE 1

| Num. | Gonio | d | Int | I/Imax |
|---|---|---|---|---|
| 1 | 3.1471 | 28.0519 | 459 | 40.9 |
| 2 | 5.4771 | 16.1222 | 173 | 15.4 |
| 3 | 6.3113 | 13.9931 | 1123 | 100.0 |
| 4 | 8.3399 | 10.5934 | 651 | 58.0 |
| 5 | 9.4584 | 9.34306 | 68 | 6.1 |
| 6 | 10.9249 | 8.09192 | 521 | 46.4 |
| 7 | 11.3641 | 7.78021 | 202 | 18.0 |
| 8 | 13.7493 | 6.43537 | 673 | 59.9 |
| 9 | 14.4568 | 6.12201 | 653 | 58.1 |
| 10 | 16.7047 | 5.30289 | 218 | 19.5 |
| 11 | 17.5820 | 5.04021 | 141 | 12.6 |
| 12 | 18.0665 | 4.90613 | 85 | 7.6 |
| 13 | 18.6183 | 4.76195 | 123 | 10.9 |
| 14 | 19.2225 | 4.61361 | 159 | 14.1 |
| 15 | 19.6709 | 4.50945 | 225 | 20.1 |
| 16 | 21.1502 | 4.19726 | 113 | 10.1 |
| 17 | 22.1846 | 4.00385 | 133 | 11.8 |
| 18 | 22.5526 | 3.93933 | 218 | 19.4 |
| 19 | 22.9545 | 3.87127 | 156 | 13.9 |
| 20 | 23.8541 | 3.72726 | 80 | 7.2 |
| 21 | 25.1254 | 3.54148 | 88 | 7.9 |
| 22 | 26.0485 | 3.41803 | 137 | 12.2 |
| 23 | 26.2865 | 3.38763 | 142 | 12.6 |
| 24 | 26.6647 | 3.34043 | 95 | 8.5 |
| 25 | 27.4234 | 3.24971 | 82 | 7.3 |
| 26 | 28.5340 | 3.1257 | 54 | 4.8 |
| 27 | 31.2898 | 2.85641 | 90 | 8.0 |
| 28 | 32.6019 | 2.74438 | 42 | 3.8 |
| 29 | 35.6160 | 2.51873 | 38 | 3.4 |
| 30 | 36.9104 | 2.43332 | 41 | 3.6 |
| 31 | 37.8432 | 2.37546 | 31 | 2.8 |
| 32 | 38.9515 | 2.31038 | 35 | 3.1 |
| 33 | 45.8241 | 1.97859 | 27 | 2.4 |

Figure 2:
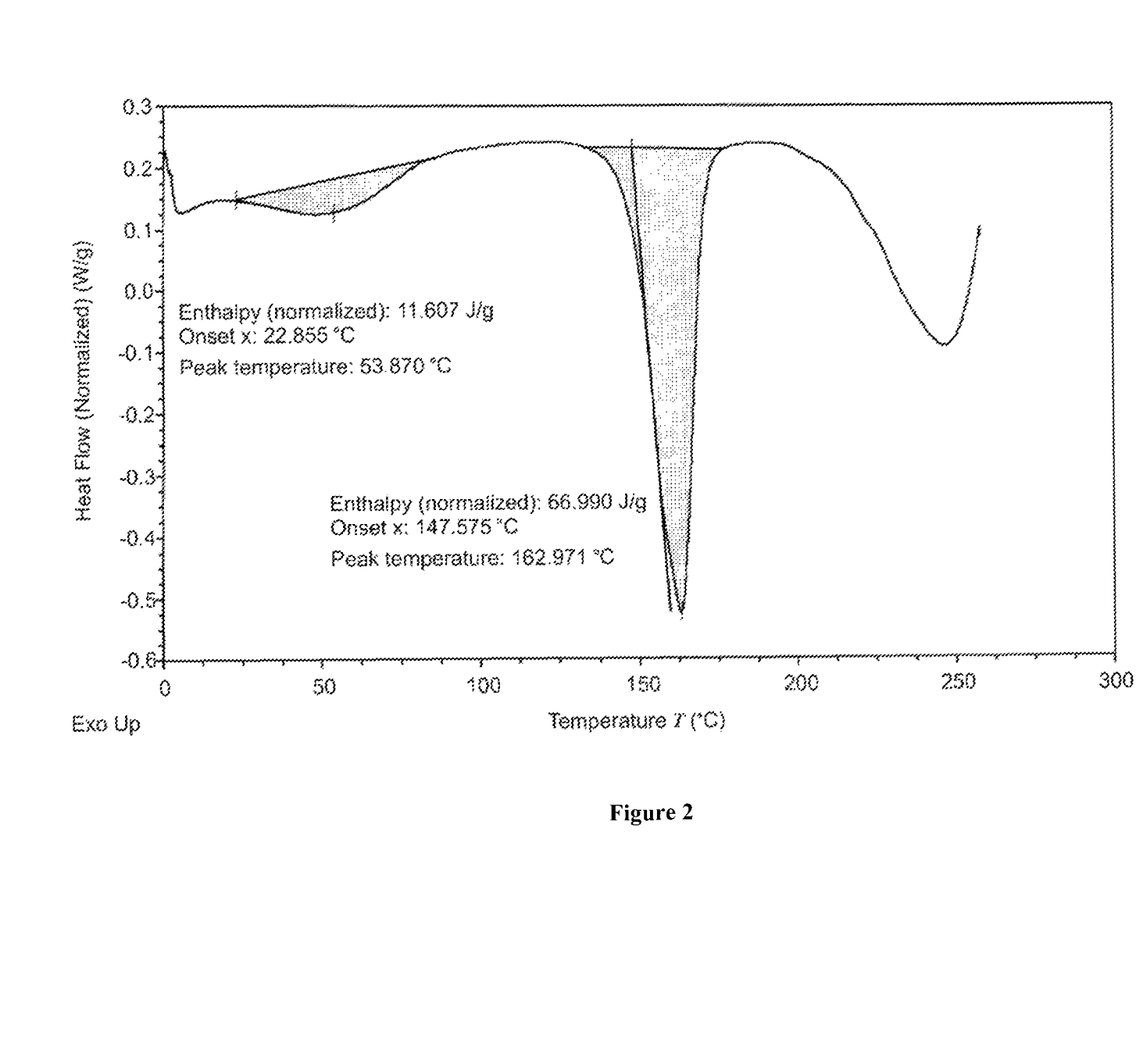

In another aspect of the present invention, is novel crystalline form B1 Linagliptin intermediate of Formula V is further characterized by DSC having endotherms at around 53.87° C. & 163° C. and the DSC pattern in accordance with the FIG. 2.

Figure 3:
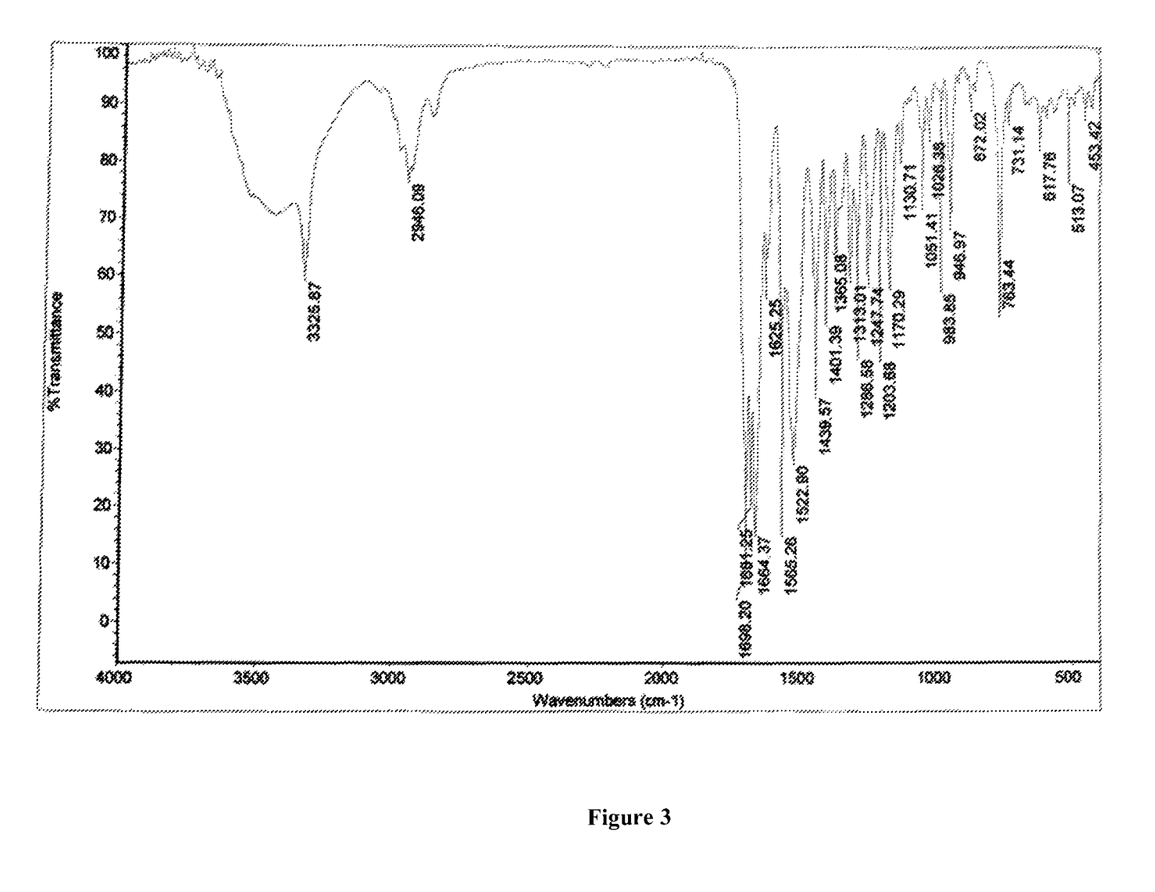

In another aspect of the present invention, the novel crystalline form B1 Linagliptin intermediate of Formula V is further characterized by FT-IR and the FT-IR pattern is in accordance with the FIG. 3.

Figure 4:
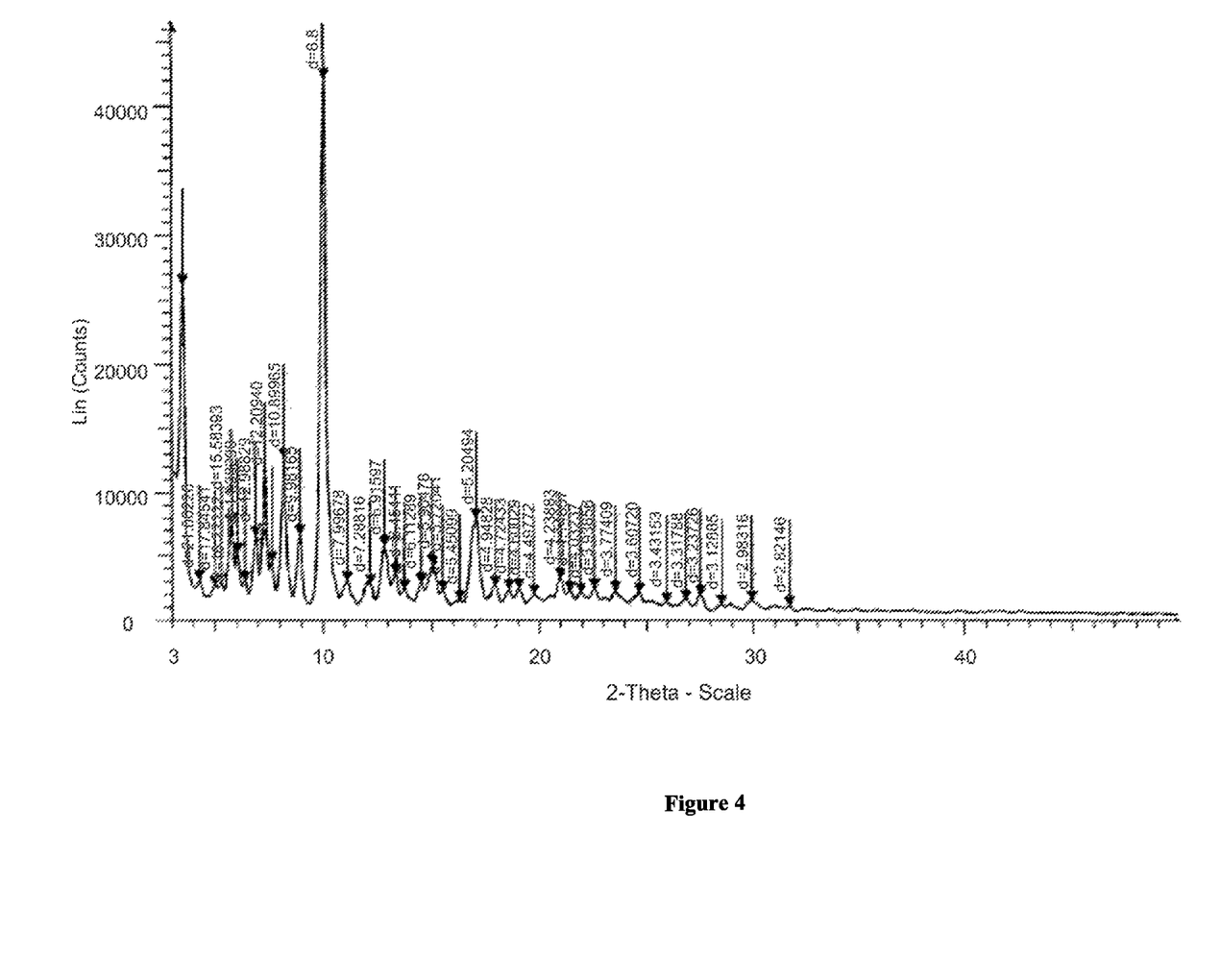
FIG. 4: Illustrates the PXRD pattern of novel crystalline Linagliptin intermediate of Formula V as obtained from Step 2 of Example-2b.

In another aspect of the present invention, the novel crystalline form B2 Linagliptin intermediate of Formula V is further characterized by PXRD having few prominent 2-theta values at 3.43±0.2, 8.10±0.2, 9.96±0.2 & 17.02±0.2 degrees 2θ and the PXRD pattern in accordance with the FIG. 4.

TABLE 2

| Num. | Gonio | d | Int | I/Imax |
|---|---|---|---|---|
| 1 | 3.4322 | 25.722 | 1128 | 61.9 |
| 2 | 4.2038 | 21.0023 | 128 | 7.0 |
| 3 | 4.9479 | 17.8454 | 109 | 6.0 |
| 4 | 5.2243 | 16.9019 | 119 | 6.6 |
| 5 | 5.6738 | 15.5639 | 318 | 17.5 |
| 6 | 5.9819 | 14.7629 | 218 | 12.0 |
| 7 | 6.3135 | 13.9882 | 124 | 6.8 |
| 8 | 6.8103 | 12.9688 | 276 | 45.2 |
| 9 | 7.2345 | 12.2094 | 410 | 22.5 |
| 10 | 7.5566 | 11.6896 | 188 | 10.3 |
| 11 | 8.1050 | 10.8998 | 542 | 29.7 |
| 12 | 8.8520 | 9.98165 | 281 | 15.5 |
| 13 | 9.9569 | 8.87638 | 1821 | 100.0 |
| 14 | 11.0533 | 7.99678 | 125 | 6.8 |
| 15 | 12.1341 | 7.28816 | 114 | 6.3 |
| 16 | 12.7897 | 6.91597 | 243 | 13.3 |
| 17 | 13.2897 | 6.65688 | 149 | 8.2 |
| 18 | 13.7092 | 6.45411 | 94 | 5.2 |
| 19 | 14.4782 | 6.11299 | 117 | 6.4 |
| 20 | 14.9916 | 5.90478 | 179 | 9.8 |
| 21 | 15.4777 | 5.72041 | 90 | 4.9 |
| 22 | 16.2478 | 5.45099 | 58 | 3.2 |
| 23 | 17.0214 | 5.20494 | 336 | 18.5 |
| 24 | 17.9187 | 4.94626 | 107 | 5.9 |
| 25 | 18.5696 | 4.77433 | 94 | 3.2 |
| 26 | 19.0284 | 4.66023 | 97 | 5.3 |
| 27 | 19.7227 | 4.49772 | 77 | 4.2 |
| 28 | 20.9405 | 4.23883 | 133 | 7.3 |
| 29 | 21.4015 | 4.14859 | 88 | 4.8 |
| 30 | 21.9146 | 4.05257 | 83 | 4.5 |
| 31 | 22.5572 | 3.93855 | 98 | 5.4 |
| 32 | 23.5539 | 3.77409 | 90 | 4.9 |
| 33 | 24.660 | 3.60726 | 84 | 4.6 |
| 34 | 25.9442 | 3.43153 | 53 | 2.9 |
| 35 | 26.8485 | 3.31798 | 61 | 3.3 |
| 36 | 27.5309 | 3.23726 | 76 | 4.2 |
| 37 | 28.5232 | 3.12685 | 44 | 2.4 |
| 38 | 29.9254 | 2.98346 | 58 | 3.2 |
| 39 | 31.6875 | 2.82146 | 39 | 2.2 |

Figure 5:
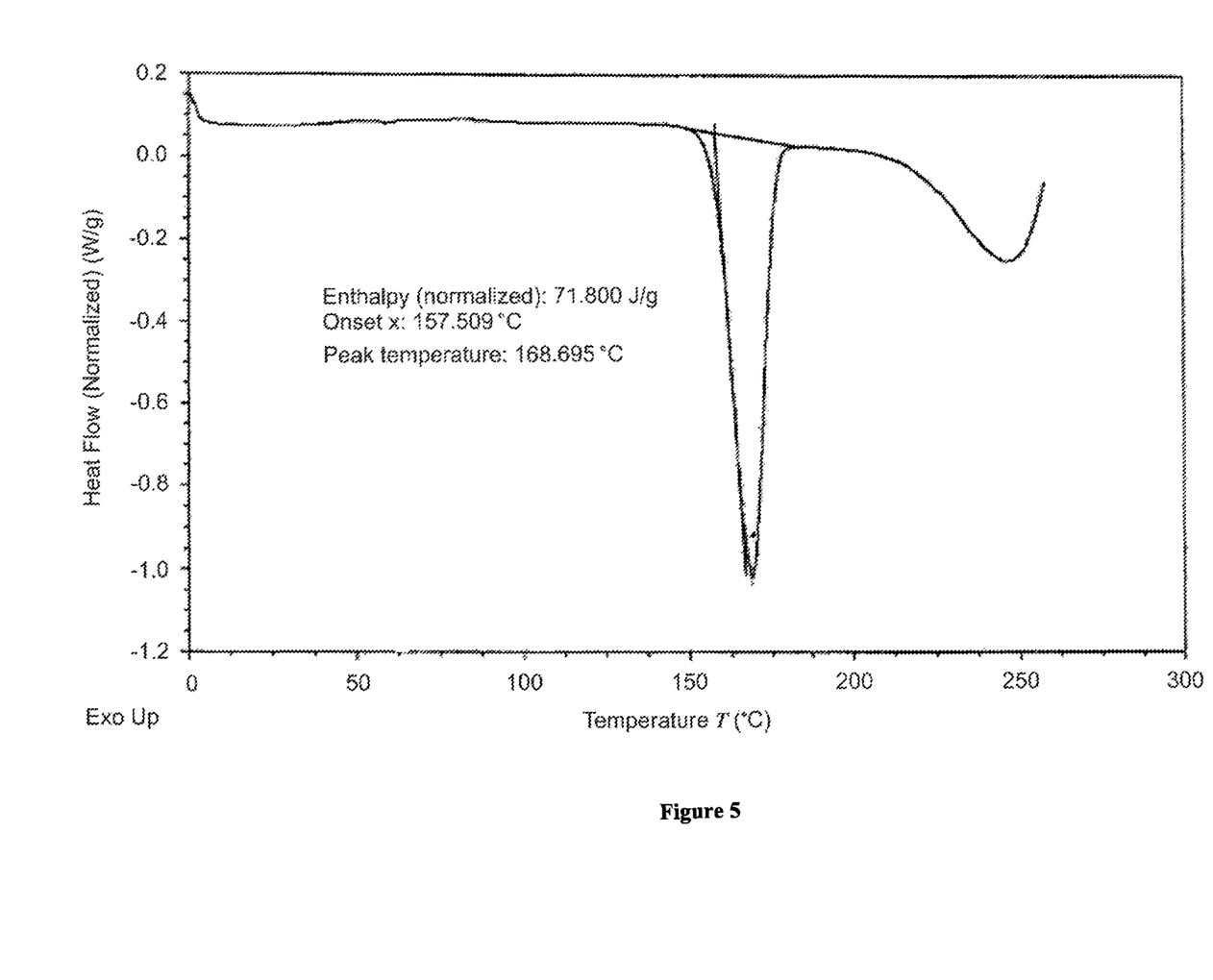
FIG. 5: Illustrates the DSC thermogram of novel crystalline Linagliptin intermediate of Formula V as obtained from Step 2 of Example-2b.

In another aspect of the present invention, is novel crystalline form B2 Linagliptin intermediate of Formula V is further characterized by DSC having endotherm at around 168.69° C. and the DSC pattern in accordance with the FIG. 5.

According to another aspect of the present invention provides process for the preparation of anhydrous form AB of Linagliptin.

Characterization Techniques

FT-IR, DSC and PXRD techniques were used for characterising the co-crystal. The infrared spectroscopy, presents a great quantity of information about the chemical bonds and interaction. It is a fast analysis method, non-destructive.

The Powder X-ray diffraction is one of the most used techniques to determine different crystalline structures. This technique can distinguish the presence of a new crystallographic motif, which can be a polymorph or a co-crystal. It is a non-destructive method and presents diffractions patterns unique for each structure.

The differential scanning calorimetry is a characterization method based on the heat of reaction involved in different thermal events. For the pharmaceutical industry, the DSC is mostly used to obtain melting points of the API and thus, determine its purity.

Instrumental Parameters

DSC was performed on a Discovery DSC (TA instruments). About 3-5 mg of sample placed in crimped aluminium sample pan to be positioned on auto sampler. The temperature range was from 30-350° C. @ 10° C./min. Samples were purged by a stream of nitrogen flowing at 50 mL/min.
Equilibrate: 30° C.
Ramp: 10° C./min
Range: 30° C.-350° C.
The FT-IR spectrum (Fourier transform R spectroscopy) was recorded using the Fisher Scientific (NICOLET-iS50-FTIR), equipped with a KBr splitter and a DTGS KBr detector. The spectrum was recorded in the range of 4000 cm-1 to 400 cm-1

The powder X-ray powder diffractogram (XRPD) was obtained by using the instrument XRD BRUKER D8 ADVANCE, equipped with LYNXEYE detector with 40 mA current intensity and 40 kV voltage.
The sample was arranged on a Si-Zero background Sample holder and analysed using the following parameters:
Scanning range)(°: 3.000 to 60.000
Step size)(°: 0.03
Scan type: Locked coupled
Scanning mode: continuous
Count time per step (s): 0.5
Delay time (s): 0
Divergent slit: 0.300
Antiscatter slit: 0.300

Advantages of Present Invention

An API can exist in a variety of solid state forms, which include: polymorphs; solvates; hydrates; salts; co-crystals and amorphous forms. Each form exhibits unique physiochemical properties that can profoundly influence the bioavailability, stability, manufacturability and other performance characteristics of the Formulated API.

Crystalline forms when compared to the amorphous form often show desired unique physical and/or biological characteristics which usually contributes in the manufacture or Formulation of the active compound, to the purity levels and uniformity required for regulatory approval. Hence, it is desirable to provide the pharmaceutically active ingredient in a substantially pure, crystalline and stable form of API.

Furthermore, the provision of further crystalline forms of a pharmaceutically useful compound offers an opportunity to improve the performance profile of a pharmaceutical product. In particular, not all solid forms of a pharmaceutically useful compound are equally suited for development of a pharmaceutical dosage form. It is therefore desirable to widen the reservoir of materials a Formulation scientist can select from, such that he can design a new dosage form of a drug having improved characteristics.

BRIEF DESCRIPTION OF THE FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure wherein:

FIG. 1: Illustrates the PXRD pattern of novel crystalline Linagliptin intermediate of Formula V as obtained from Step 2 of Example-2a.

FIG. 2: Illustrates the DSC thermogram of novel crystalline Linagliptin intermediate of Formula V as obtained from Step 2 of Example-2a.

FIG. 3: Illustrates the FT-IR of novel crystalline Linagliptin intermediate of Formula V as obtained from Step 2 of Example-2a.

The method of analysis of the compounds represented in the figures as above are as below:

PXRD Analysis

About 300 mg of powder sample was taken onto the sample holder and was tightly packed on the sample holder uniformly by means of glass slide and Powder X-ray diffraction was recorded on Bruker D8 Advance diffractometer (Bruker-AXS, Karlsruhe, Germany) using Cu-Kα X-radiation ($\lambda$=1.5406 Å) at 40 kV and 30 mA powder. X-ray diffraction patterns were collected over the 2θ range 3-50° at a scan rate of 1°/min.

DSC Analysis

DSC was performed on a Mettler Toledo DSC 822e module. 4-6 mg of sample was placed in crimped but vented aluminium sample pans. The temperature range was from 30-250° C. @ 10° C./min. Samples were purged by a stream of nitrogen flowing at 80 mL/min.

IR Analysis

IR was performed on a Fisher Scientific (NICOLET-iS50-FTIR). About 5 mg of sample was spread over the region of diamond ATR sampling station and collected the sample spectrum between 4000 cm-1 to 400 cm-1 to obtain a spectrum of suitable intensity (above 60% transmission at 2000 cm-1).

DETAILED DESCRIPTION OF THE INVENTION

The embodiments of the present invention are further described using specific examples herein after. The examples are provided for better understanding of certain embodiments of the invention and not, in any manner, to limit the scope thereof. Possible modifications and equivalents apparent to those skilled in the art using the teachings of the present description and the general art in the field of the invention shall also form the part of this specification and are intended to be included within the scope of it.

Synthetic Scheme of the Present Invention:

-continued

Formula V

Stage-3

Formula V

TFA/MDC
Aq. ammonia
MTBE
Charcoal
Water
→

LINAGLIPTIN

Example 1: Preparation of 8-bromo-7-(but-2-yn-1-yl)-3-methyl-1-((4-methylquinazolin-2-yl) methyl)-3,7-dihydro-1H-purine-2,6-dione (Formula III)

Formula I

Formula II

NMP/K₂CO₃
Water/Methanol/MDC
→

-continued

Formula III

To a 3000 mL glass vessel equipped with a stirrer, condenser and a thermometer probe were added Formula I (100.0 g, 0.33 mol), Formula II (70.02 g, 0.36 mol), potassium carbonate (51.16 g, 0.37 mol) and N-Methyl-2-pyrrolidone (500.0 mL, 5.00 vol) and the mass was heated to 80±2° C. The reaction mass was maintained at 80±2° C. under stirring for 6 to 8 h. The reaction mass was cooled to 25±5° C. and water (1000 mL) was added to the reaction mass under constant stirring. The mass was filtered and the solid was washed with water (200 mL) followed by Methanol (200 mL), suck dried and dried at 45±5° C. under vacuum for 8-10 h to obtain compound of Formula III as a pale yellow solid. It is further purified using a mixture of methanol and MDC.

Example 2a: Preparation of tert-butyl (R)-(1-(7-(but-2-yn-1-yl)-3-methyl-1-((4-methylquinazolin-2-yl)methyl)-2,6-dioxo-2,3,6,7-tetrahydro-1H-purin-8-yl) piperidin-3-yl) carbamate (Formula V)

To a 3000 mL glass vessel equipped with a stirrer, condenser and a thermometer probe were added Formula III (100.0 g, 0.22 mol) Formula IV (50.81 g, 0.25 mol), potassium iodide (3.66 g, 0.02 mol), potassium carbonate (36.65 g, 0.26 mol) and DMSO (400 mL). The mass was heated to 82±2° C. The reaction mass was maintained at 82±2° C. under stirring for 6-9 h. The reaction mass was cooled to 25±5° C., MDC (400 mL) & water (600 mL) was added to the reaction mass under constant stirring for 1 to 2 h. Layers were separated. Re-extracted the aqueous layer with MDC (2×200 mL). Combined the MDC layers and washed with water (200 mL). Separated the layers and partially concentrated the MDC layer to obtain the Formula V in MDC solution.

Purification of Crude Formula V:

To the compound of Formula V in MDC solution was added acetonitrile and concentrated. Added another lot of acetonitrile and heated the reaction mass to 78±3° C. for 2 h. Charge water at temperature 70±5° C. Maintain at 75±5° C. for 2 hours. Reaction mass was slowly cooled to 25±5° C. Stir the mass for 1 hour at 25±5° C. The resulting product was filtered off, washed with acetonitrile followed by water, suck dried and dried at 70±5° C. under vacuum for 16-18 h to obtain compound of Formula V as a pale yellow solid.

The novel crystalline Linagliptin intermediate of Formula V which is prepared as per Example-2 is characterized by XPRD as represented in FIG. 1.

The novel crystalline Linagliptin intermediate of Formula V which is prepared as per Example-2 is characterized by DSC as represented in FIG. 2.

The novel crystalline Linagliptin intermediate of Formula V which is prepared as per Example-2 is characterized by FTIR as represented in FIG. 3.

Example 2b: Preparation of tert-butyl (R)-(1-(7-(but-2-yn-1-yl)-3-methyl-1-((4-methylquinazolin-2-yl)methyl)-2,6-dioxo-2,3,6,7-tetrahydro-1H-purin-8-yl) piperidin-3-yl) carbamate (Formula V)

To a 3000 mL glass vessel equipped with a stirrer, condenser and a thermometer probe were added Formula III (100.0 g, 0.22 mol) Formula IV (50.81 g, 0.25 mol), potassium iodide (3.66 g, 0.02 mol), potassium carbonate (36.65 g, 0.26 mol) and DMSO (400 mL). The mass was heated to 82±2° C. The reaction mass was maintained at 82±2° C. under stirring for 6-9 h. The reaction mass was cooled to 25±5° C., MDC (400 mL) & water (600 mL) was added to the reaction mass under constant stirring for 1 to 2 h. Layers were separated. Re-extracted the aqueous layer with MDC (2×200 mL). Combined the MDC layers and washed with water (200 mL). Separated the layers and partially concentrated the MDC layer to obtain the Formula V in MDC solution.

Purification of Crude Formula V:

To the compound of Formula V in MDC solution was added pre-heated (60° C.) Acetonitrile (800 mL) was charged to the crude Formula V, heated the reaction mass to 55±5° C. and added water (500 mL). The reaction mixture was heated to 70±5° C. and stirred for 2-4 h and cooled the reaction mass slowly to room temperature. Stirred the reaction mass for 1 h at 25±5° C. The mass was filtered and the solid was washed with Acetonitrile (60 mL) followed by water (140 mL), suck dried and dried at 70±5° C. under vacuum for 16-18 h to obtain compound of Formula V as a pale yellow solid.

The novel crystalline Linagliptin intermediate of Formula V which is prepared as per Example-2 is characterized by XPRD as represented in FIG. 4.

The novel crystalline Linagliptin intermediate of Formula V which is prepared as per Example-2 is characterized by DSC as represented in FIG. 5.

Example 3: Preparation of Linagliptin

Formula V

LINAGLIPTIN

To a 3000 mL glass vessel equipped with a stirrer, condenser and a thermometer probe were added Formula V (100.0 g, 0.17 mol) and MDC (600 mL, 6.0 vol), stirred to dissolve at 25±5° C. The reaction mixture was cooled to 20±5° C. and TFA (200 mL, 2.0 vol) was added slowly and warmed to 25±5° C. and stirred for 6-8 h. After completion of the reaction MDC (500 mL) was added and cooled the reaction mass to 3±3° C., water (500 mL) pre-chilled to 5±3° C. was added and adjusted pH of the reaction mass to 9 to 11 using aq. Ammonia maintaining the reaction temperature at 5±3° C. The reaction mass was warmed to 25±5° C. and stirred for 2 h. Layers were separated and MDC layer was preserved. The aqueous layer was re-extracted with MDC (300 mL). Combined MDC layers were treated with activated charcoal and stirred for 30 min. The reaction mass was filtered over celite bed and washed the celite bed with MDC (200 mL). Filtrate as obtained was concentrated at a temperature below 45° C. up to 3.0 vol. with respect to weight of Formula V used as input. MTBE (1200 mL) was added dropwise at 25±5° C. to the partially concentrated product and stirred for 1 h. The reaction mass was further cooled to 5±3° C. and stirred for 2 h. The product as obtained was filtered off, washed with MTBE (200 mL) and suck dried. The product was dried at 45±5° C. under vacuum for 10 h to obtain Linagliptin as a pale yellow solid. The product was kept at −5±5° C. for 36 h, raised the temperature to 25±5° C. and hold it for 4-5 h to obtain anhydrous crystalline form A/B of Linagliptin.

Figure 6:
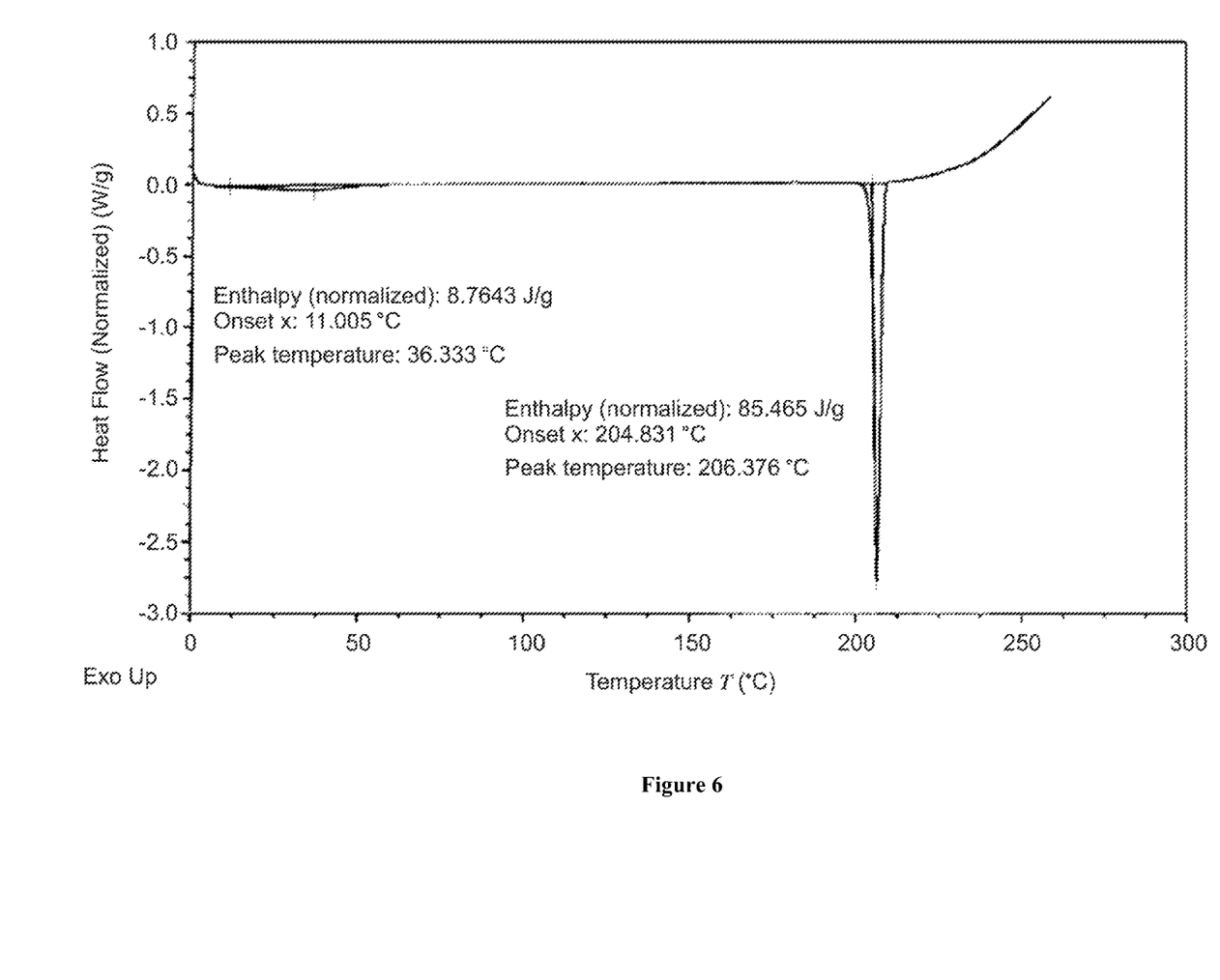
FIG. 6: Illustrates the DSC thermogram of anhydrous form A/B of Linagliptin as obtained from Step 3 of Example-3.

The anhydrous crystalline form A/B of Linagliptin which is prepared as per Example-3 is characterized by DSC as represented in FIG. 6.

The invention claimed is:

1. A crystalline form B1 of Linagliptin intermediate of formula V,

Formula-V characterised by an XPRD pattern in accordance with FIG. 1.

2. The crystalline form B1 of Linagliptin intermediate of formula V, of claim 1 having prominent peaks at 3.14±0.2, 6.31±0.2, 8.34±0.2, 10.93±0.2, 13.75±0.2 & 14.46±0.2 degrees 2θ.

3. The crystalline form B1 of Linagliptin intermediate of formula V, of claim 1 having DSC endotherms at 53.87 & 162.97° C.

4. The process for preparation of crystalline form B1 of Linagliptin intermediate of formula V, of claim 1 comprising following steps of:
   a. Heating crude linagliptin intermediate of formula V in a solvent,
   b. Adding a suitable anti-solvent to the reaction mass of above step at elevated temperature,
   c. Heating the reaction mass to an elevated temperature,
   d. Reaction mass was cooled and isolated the crystalline form of Linagliptin intermediate of formula V.

5. The process for preparation of claim 4, wherein solvent is acetonitrile.

6. The process for preparation of claim 4, wherein anti-solvent is water.

7. A crystalline form B2 of Linagliptin intermediate of formula V,

Formula-V characterised by an XPRD pattern in accordance with FIG. 4.

8. The crystalline form B2 of Linagliptin intermediate of formula V, of claim 7 having prominent peaks at 3.43±0.2, 8.10±0.2, 9.96±0.2 & 17.02±0.2 degrees 2θ.

9. The crystalline form B2 of Linagliptin intermediate of formula V, of claim 7 having a DSC endotherm at 168.69° C.

10. The process for preparation of crystalline form B2 of Linagliptin intermediate of formula V, of claim 7 comprising following steps of:
   a. Treating crude linagliptin intermediate of formula V with preheated solvent,
   b. Adding an anti-solvent to the reaction mass of above step,
   c. Heating the reaction mass to an elevated temperature,
   d. Reaction mass was cooled and isolated the crystalline form of Linagliptin intermediate of formula V.

* * * * *